United States Patent [19]

Arison et al.

[11] 4,285,963

[45] Aug. 25, 1981

[54] NOVEL DERIVATIVES OF C-076 COMPOUNDS

[75] Inventors: Byron H. Arison, Watchung; Robert T. Goegelman, Linden; Vincent P. Gullo, Edison, all of N.J.

[73] Assignee: Merck & Co., Inc., Rahway, N.J.

[21] Appl. No.: 175,615

[22] Filed: Aug. 7, 1980

[51] Int. Cl.$^3$ .................. A61K 31/365; C07D 493/20; C07D 313/06

[52] U.S. Cl. .............................. 424/279; 260/343.41; 435/76; 435/119; 536/17 R; 424/181

[58] Field of Search .................. 260/343.41; 424/279

[56] References Cited

U.S. PATENT DOCUMENTS

| | | | |
|---|---|---|---|
| 3,950,360 | 4/1976 | Aoki et al. | 260/343.41 |
| 4,093,629 | 6/1978 | Fisher | 260/343.41 |
| 4,171,314 | 10/1979 | Chabala et al. | 260/343.41 |
| 4,173,571 | 11/1979 | Chabala et al. | 260/343.41 |

FOREIGN PATENT DOCUMENTS

2345/77 of 1977 South Africa.

*Primary Examiner*—Henry R. Jiles
*Assistant Examiner*—Jane T. Fan
*Attorney, Agent, or Firm*—David L. Rose; Harry E. Westlake

[57] ABSTRACT

There are disclosed certain new derivatives of C-076 compounds which have been isolated from the fermentation broth that produced the original C-076 compounds. The compounds retain the C-076 16-membered cyclic backbone, however, the groups attached thereto are considerably modified from the original C-076 compounds. The new compounds have been found to retain the biological activity of the parent C-076 compounds. The compounds are thus potent antiparasitic agents and compositions and methods for such uses are also disclosed.

9 Claims, No Drawings

NOVEL DERIVATIVES OF C-076 COMPOUNDS

BACKGROUND OF THE INVENTION

The C-076 family of compounds are a series of macrolides isolated from the fermentation broth of a strain of *Streptomyces avermitilis*. The C-076 compounds are characterized by having a 16-membered cyclic backbone substituted with a disaccharide and having a bicyclic spiroketal fused thereon. The compounds have the structure:

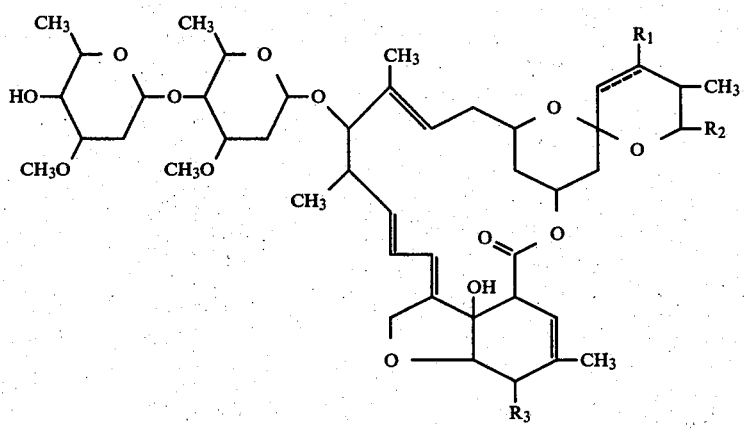

wherein the broken line indicates a single or a double bond; $R_1$ is hydroxy and is present only when said broken line indicates a single bond;
$R_2$ is iso-propyl or sec-butyl; and
$R_3$ is methoxy or hydroxy.

The C-076 compounds are named using a system of designations which corresponds to the structural variations as is set forth in the following table.

| Compound | $R_1$ | $R_2$ | $R_3$ |
| --- | --- | --- | --- |
| A1a | Double bond | sec-butyl | —$OCH_3$ |
| A1b | Double bond | iso-propyl | —$OCH_3$ |
| A2a | —OH | sec-butyl | —$OCH_3$ |
| A2b | —OH | iso-propyl | —$OCH_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

The above compounds are isolated from the fermentation broth of *Streptomyces avermitilis* using normal extraction and isolation procedures. The C-076 producing culture and the morphological characteristics thereof along with the procedures used for separating and isolating the C-076 compounds, are fully described in South Africa Pat. No. 77/2345, published Apr. 3, 1979.

The fermentation is carried out in an aqueous medium and includes an assimilable source of carbon, an assimilable source of nitrogen and inorganic salts and the fermentation is generally carried out under aerobic conditions. The specific nutrients and parameters for the fermentation are described completely in the above cited South African Patent.

The C-076 producing culture and a mutant thereof have been deposited in the permanent culture collection of the American Type Culture Collection, 12301 Parklawn Drive, Rockville, Maryland 20852. The cultures are accessible under the accession numbers ATCC 31267 for the basic culture and ATCC 31272 (lyophilized tube) and ATCC 31271 (frozen vial) for the mutant. The C-076 compounds are potent antiparasitic agents with very broad spectrum anthelmintic, acaricidal, nematocidal and insecticidal activity.

SUMMARY OF THE INVENTION

The instant invention is concerned with novel C-076 derivatives and procedures for their isolation from the fermentation broth of a C-076 producing strain of *Streptomyces avermitilis*. Thus, it is an object of this invention to describe such novel C-076 derivatives. It is a further object of this invention to describe the processes for their isolation from fermentation broths. A still further object is to describe the antiparasitic effects of such novel compounds. Further objects will become apparent from a reading of the following description.

DESCRIPTION OF THE INVENTION

The novel compounds of this invention are best described in the following three structural formulae:

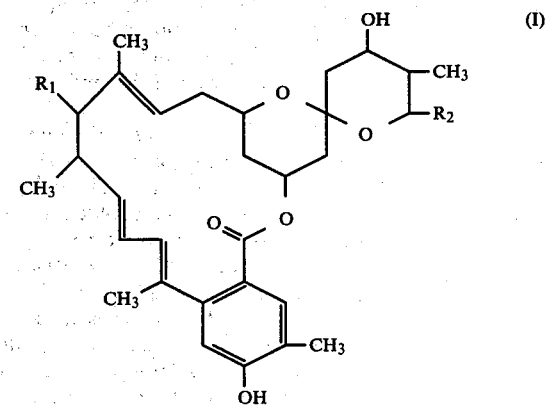

(I)

wherein (a) $R_1$ is —OH and $R_2$ is sec-butyl; (b) $R_1$ is =O and $R_2$ is sec-butyl; (c) $R_1$ is —OH and $R_2$ is iso-propyl;

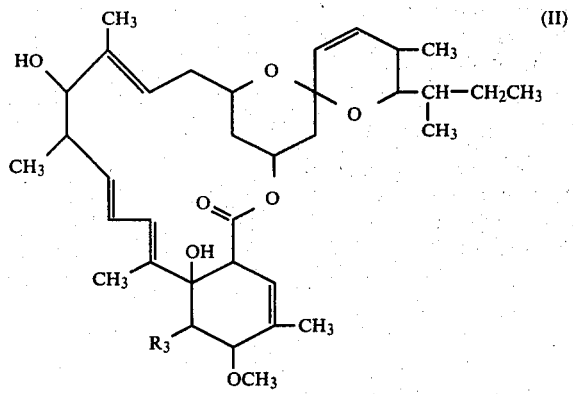

wherein $R_3$ is (a) hydrogen or (b) hydroxyl;

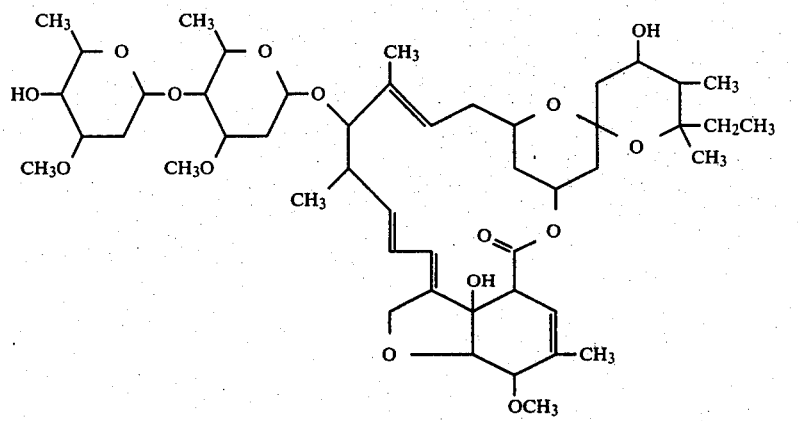

From an analysis of the foregoing six compounds, they are seen to be similar to the parent C-076 compounds, but with some very major differences.

In structure I the C-076 furan ring is opened and the 6-membered ring is aromatized. In addition, the disaccharide group has been removed.

In structure II the furan ring is again opened, but the 6-membered ring is not aromatized. The disaccharide group of the parent C-076 compounds is also removed.

In structure III all of the major functions of the C-076 compounds are retained but the 25-position substituents are different, being 2 groups, a methyl and an ethyl, rather than a single sec-butyl or iso-propyl group.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intesinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, perferably of the vegetable oil variety such as peanut oil, cotton seed oil and the like. Other parenteral vehicles such as organic preparation using solketal, glycerol, formal and aqueous parenteral formulations are also used. The active C-076 compound or compounds are dissolved or suspended in the parenteral formulation for administration; such formulations generally contain from 0.005 or 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg. per kg. of animal body weight, such total dose being given at one time or in divided doses over a relatively short period of time such as 1–5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distiller's dried grains, corn meal, citrus meal, fermentation residues, ground oyster shells, wheat shorts, molasses solubles, corn cob meal edible bean mill feed, soya grits, crushed limestone and the like. The active C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount of give the finished feed the concentration of active compound desired for the treatment and control of parasitic diseases. Although the desired concentration of active compound will vary depending upon the factors previously mentioned as well as upon the particular C-076 compound employed, the compounds of this invention are usually fed at concentrations of between 0.00001 to 0.002% in the feed in order to achieve the desired antiparasitic result.

In using the compounds of this invention, the individual C-076 components may be isolated and purified and used in that form. Alternatively, mixtures more of the individual C-076 components may be used. It is not necessary to completely separate the various C-076 compounds obtained from the purification of the fermentation broth. Occasionally, there is obtained a mixture containing two or more of the C-076 compounds, but having other unrelated compounds excluded therefrom, and such mixture may be used for the prevention and treatment of parasitic diseases as described herein. Such a mixture generally will contain unequal proportions of the C-076 compounds, however, all of the compounds have substantial activity and the antiparasitic activity of the mixture can be accurately determined.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are isolated from the fermentation broth of *Streptomyces avermitilis* in smaller amounts than the parent C-076 compounds. However, substantially similar processes are used to isolate such compounds.

The standard techniques for extraction and purification, known to those skilled in the art, are employed to purify the instant compounds. The techniques of solvent extraction, column chromatography, thin layer chromatography, preparative layer chromatography, high pressure liquid chromatography and the like are useful for the isolation and purification of the instant compounds.

The following examples describe the fermentation and the isolation and purification procedures for the preparation of the instant compounds. The examples are provided in order that the invention might be more fully understood. They should not be construed as limitative of the invention.

EXAMPLE 1

A 250 ml. baffled Erlenmeyer flask containing 50 ml. of the following medium:
Lactose —2.0%
Distiller's solubles —1.5%
Autolyzed yeast, Ardamine pH —0.5%
pH—before sterilization —7.0
is inoculated with the contents of one frozen vial of *Streptomyces avermitilis* MA 4848 and incubated on a rotary shaker at 28° C. for 24 hours at 150 RPM.

10 ml. of the above fermentation media is employed to inoculate 500 ml. of the same medium as above in a 2 liter baffled Erlenmeyer flask. The fermentation media is incubated at 150 RPM on a rotary shaker at 28° C. for 24 hours.

All of the foregoing media is employed to inoculate 467 liters of the following media in a 756 liter stainless steel fermentor:
Lactose —2.0%
Distiller's solubles —1.5%
Autolyzed yeast, Ardamine pH —0.5%
Polyglycol 2000 —0.32 ml./liter
pH—before sterilization —7.0

The fermentation media is incubated at 28° C. for 40 hours with an air flow 10 cubic feet per minute and an agitation rate 130 RPM.

230 Liters of the above media is employed to inoculate 4,310 liters of the following medium in a 5,670 liter stainless steel fermentor:
Dextrose —4.5%
Peptonized milk —2.4%
Autolyzed yeast, Ardamine pH —0.25%
Polyglycol 2000 —2.5 ml./liter
pH—before sterilization —7.0

The fermentation continues for 144 hours at 26° C. with an air flow rate of 54.3 cubic feet per minute and agitation of 120 RPM.

The fermentation media, 4165 liters, are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The extract is evaporated to a volume of about 370 liters. The pH of the concentrate is adjusted to about 5.05 with concentrated hydrochloric acid and combined with about 387 liters of methylene chloride. The combined solvents are agitated for about 2 hours and separated. The aqueous layer is combined with an additional 580 liters of methylene chloride and agitated for about 2 hours. The layers are separated and each methylene chloride extract separately treated with about 10 kilograms of Super-Cel and filtered. Both extracts are evaporated to a combined volume of about 40 liters.

EXAMPLE 2

The 40 liter solution of C-076 in methylene chloride of the previous example is concentrated to dryness in vacuo and the residue is combined 3 times with 40 liter portions of methanol and evaporated to dryness to remove any residual methylene chloride. The final methanol concentrate volume is approximately 20 liters. The methanol solution is stored overnight and filtered. The filter cake is washed with 40 liters of fresh methanol and the methanol filtrates and washings are combined. The methanol solution is combined with 120 liters of ethylene glycol and 135 liters of heptane. One kg of sodium chloride is added. The 2 layer solution is agitated for 5 minutes and the lower layer (ethylene glycol and methanol) is separated. The heptane solution is washed with a mixture of 20 liters of ethylene glycol and 6.3 liters of methanol. After five minutes of agitation, the lower layer is separated and combined with the first ethylene glycol/methanol extract. An equal volume of water (approximately 150 liters) containing 79 g. of sodium chloride per liter is added to the ethylene glycol/methanol extracts. This solution is extracted with 150 liters of ethyl ether with agitation for 5 minutes. The ether layer is washed with 60 liters of water containing 20 g of sodium chloride per liter (⅓ volume). The solution is agitated for 5 minutes and the layers separated. This procedure is repeated an additional 2 times affording a final ether layer volume of 115 liters. The ether layer is concentrated in vacuo, to a minimum volume, keeping the temperature less than 25° C. 40 Liters of methylene chloride is added to the residue and the solution is evaporated to dryness. This procedure is repeated and the final residue concentrated in vacuo at 50° C. to dryness.

EXAMPLE 3

A 30 centimeter diameter column is prepared with a layer of 20 kilograms of activated alumina followed by a layer of 20 kilograms of activated carbon in a solution of methylene chloride. The residue from the previous example is dissolved in methylene chloride to a volume of 15 liters and applied to the column and eluted with 20 liters of methylene chloride. These fractions are discarded. A 3% solution of isopropanol and methylene chloride (12 liters of isopropanol and 388 liters of methylene chloride) is applied to the column and eluted in approximately 200 liter fractions. The combined isopropanol and methylene chloride fractions are evaporated in vacuo at a bath temperature of about 60° C. to a volume of about 3 liters. The bath temperature is reduced to about 45° C. and the extract is evaporated to dryness in vacuo. The residue is dissolved in 10 parts methylene chloride, 10 parts hexane and one part methanol to a final volume of 8 liters. This solution is applied directly to the Sephadex LH-20 column of the next example.

EXAMPLE 4

A 30 centimeter diameter column is prepared in methanol with 36 kilograms of Sephadex LH-20 (available from Pharmacia Fine Chemicals, 800 Centennial Avenue, Piscataway, New Jersey 08854) and washed with a solvent consisting of 10 parts methylene chloride, 10 parts hexane and one part methanol. One-half of the C-076 solution of Example 3 is applied to the column and the column eluted at a rate of 250 ml. per minute. Two 20 liter forecuts are collected and discarded followed by 20 two liter rich cuts (identified as fractions 1-20), followed by a single 20 liter tail cut, which is discarded. Fractions 3-9 are found to contain the C-076 A compounds.

EXAMPLE 5

The process of Example 4 is repeated on the same scale one more time and all of the fractions containing the C-076 A components (fractions 1-7) are combined and evaporated to dryness, affording 194 g of crude mixed C-076 A components. A 5.0 g aliquot of this sample is chromatographed over a one liter column containing Lichroprep $^{TM}$RP-18 (EM Reagents) equilibrated and eluted with 85% methanol/water. One hundred fifty 18 ml fractions are collected. Fractions 34-49 are combined and concentrated. This process is repeated with additional 5.0 g aliquot. Fractions 36-56 are combined and concentrated. The concentrates are combined to afford 2.38 g of crude mix. This material is dissolved in methanol and chromatographed over the same Lichroprep $^{TM}$RP-18 column which is now equilibrated with 75% methanol/water. The sample is eluted with 3 liters of this solvent, followed by one liter of 80% methanol/water. One hundred sixty 25 ml fractions are collected. Fractions 120-150 are combined affording 0.892 g of material. The sample is dissolved in 10 ml of methanol and a 2 ml portion is purified by injecting 0.5 ml aliquots into high pressure liquid chromatography column (HPLC). The HPLC system employs an ES Industries chromega $^{TM}$C-18 column (50 cm ×9.6 mm) and elution with 70% methanol/water. Silica gel TLC in 20% ethyl acetate/methylene chloride yields 1.05 mg of Compound I(a) and 1.17 mg of Compound III.

A 45 g aliquot of the crude mixed C-076 A components is chromatographed over a 2 liter silica gel column with a stepwise elution of ethyl acetate in methylene chloride. The fractions eluted with 5%-15% ethyl acetate/methylene chloride are combined to yield 1.8 g of material. The fractions eluted with 50% ethyl acetate/methylene chloride thru ethyl acetate are combined to yield 6.0 g of material.

The 1.8 g sample is applied to six preparative silica gel plates and developed with 20% ethyl acetate/methylene chloride. Two fractions are collected containing 308 mg and 314 mg of material. The 308 mg sample is dissolved into 3 ml of methanol and purified in 5 runs on the HPLC using an ES Industries Chromega $^{TM}$ C-18 column. Elution is achieved with 70% methanol/water. Three fractions are collected. One fraction contains 28.8 mg of Compound II(b) and needs no further purification. The remaining two fractions, 16.7 mg and 23.8 mg, are further purified by silica gel TLC using 15% ethyl acetate/methylene chloride as the developing solvent. The 16.7 mg sample yields 4.65 mg of Compound I(b) and the 23.8 mg fraction yields 17.9 mg of Compound II(a). The 314 mg sample is dissolved into 3 ml of methanol and purified in 5 runs on the HPLC using an ES Industries Chromega $^{TM}$ C-18 column. Elution is achieved with 70% methanol/water. Preparative TLC of the 22 mg rich cut with 20% ethyl acetate/methylene chloride as the developing solvent affords 3.9 mg of Compound I(c).

What is claimed is:

1. A compound having the formula:

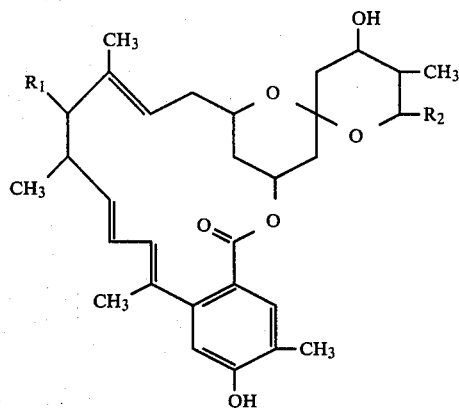

wherein (a) $R_1$ is —OH and $R_2$ is sec-butyl; (b) $R_1$ is =O and $R_2$ is sec-butyl; (c) and $R_1$ is —OH and $R_2$ is iso-propyl.

2. The compound of claim 1 wherein $R_1$ is =OH and $R_2$ is sec-butyl.

3. The compound of claim 1 wherein $R_1$ is =O and $R_2$ is sec-butyl.

4. The compound of claim 1 wherein $R_1$ is —OH and $R_2$ is iso-propyl.

5. A compound having the formula:

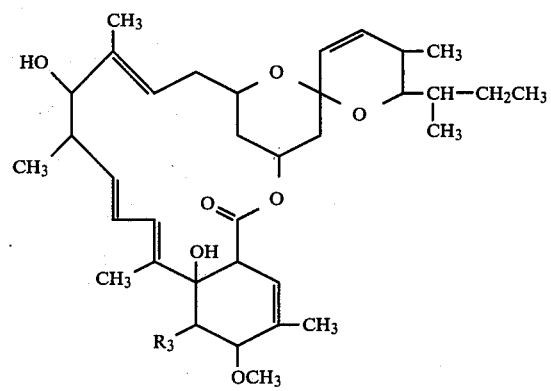

wherein $R_3$ is hydrogen of hydroxyl.

6. The compound of claim 5 wherein $R_3$ is hydrogen.

7. The compound of claim 5 wherein $R_3$ is hydroxyl.

8. A composition useful for the prevention and treatment of parasitic diseases which comprises an inert carrier having an effective amount of a compound of claim 1 or 5 incorporated therein.

9. A method for the treatment of parasitic infections which comprises administering to an animal infected with parasitic infection, an effective amount of a compound of claim 1 or 5.

* * * * *